United States Patent [19]

Perrot et al.

[11] Patent Number: 4,550,179

[45] Date of Patent: Oct. 29, 1985

[54] N-(1-ALLYL-2-PYRROLIDINYL-METHYL) 2-METHOXY-4-AMINO-5-METHYLSUL-FAMOYL BENZAMIDE

[75] Inventors: Jacques Perrot; Michel Thominet, both of Paris, France

[73] Assignee: Societe d'Etudes Scientifiques et Industrielles de l'Ile-de France, Paris, France

[21] Appl. No.: 466,573

[22] Filed: Feb. 15, 1983

Related U.S. Application Data

[63] Continuation of Ser. No. 296,164, Aug. 25, 1981, Pat. No. 4,405,636.

[30] Foreign Application Priority Data

Aug. 28, 1980 [FR] France .................. 80 18635

[51] Int. Cl.$^4$ .................. A61L 31/40; C07D 207/09
[52] U.S. Cl. .................................................. 548/571
[58] Field of Search .................................. 548/571

[56] References Cited

U.S. PATENT DOCUMENTS

| 3,219,528 | 11/1965 | Thominet | 167/65 |
|---|---|---|---|
| 3,342,826 | 9/1967 | Miller et al. | 260/326.47 |
| 3,766,178 | 10/1973 | Thominet | 260/243 B |
| 3,862,139 | 1/1975 | Podesva et al. | 260/326.47 |
| 3,975,434 | 8/1976 | Bulteau et al. | 260/326.47 |
| 4,029,673 | 6/1977 | Bulteau et al. | 260/326.47 |
| 4,197,243 | 4/1980 | Murakami et al. | 260/326.47 |
| 4,210,660 | 9/1980 | Takashima et al. | 260/326.47 |
| 4,248,885 | 2/1981 | Thominet et al. | 424/274 |
| 4,364,867 | 12/1982 | Thominet et al. | 548/567 |

FOREIGN PATENT DOCUMENTS

| 5916M | 1/1966 | France . | |
| 130957 | 10/1980 | Japan | 260/326.47 |
| 1364231 | 8/1974 | United Kingdom . | |

OTHER PUBLICATIONS

Speight et al., *Drugs*, vol. 3, pp. 159-203, (1972).
Raskin, Ann. Rev. Pharmacol. Toxicol. 21, (1981), pp. 463-478.

*Primary Examiner*—Mark L. Berch
*Attorney, Agent, or Firm*—Fitzpatrick, Cella, Harper & Scinto

[57] ABSTRACT

N-(1-allyl-2-pyrrolidinyl-methyl) 2-methoxy-4-amino-5-methylsulfamoyl benzamide and derivatives thereof, which are useful in the treatment of anomalies in cerebral hemodynamics of patients subject to migraines.

1 Claim, No Drawings

N-(1-ALLYL-2-PYRROLIDINYL-METHYL) 2-METHOXY-4-AMINO-5-METHYLSULFAMOYL BENZAMIDE

This application is a continuation of application Ser. No. 296,164 filed Aug. 25, 1981, now issued as U.S. Pat. No. 4,405,636.

The invention concerns a new benzamide, namely N-(1 allyl-2-pyrrolidinyl-methyl)2-methoxy-4-amino-5-methylsulfamoyl benzamide, a method of preparing it and its use as a medicament, particularly for basic migraine treatment. N-(1-allyl-2-pyrrolidinyl-methyl)2-methoxy-4-amino-5-methylsulfamoyl benzamide will hereinafter be referred to as the benzamide according to the invention; it has the following formula:

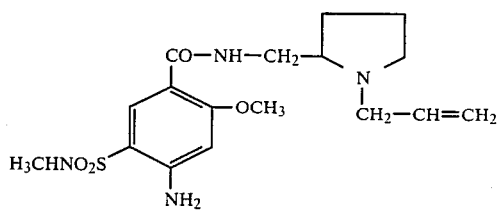

The invention covers the said benzamide according to the invention, quaternary ammonium salts of the benzamide according to the invention, N-oxides thereof, optical isomers thereof and their pharmacologically acceptable acid addition salts.

A method of obtaining the benzamide according to the invention will now be described; the starting material is methyl 2-methoxy-4-acetamino benzoate which is known in other contexts.

1. Methyl 2-methoxy-4-acetamino-5-sulfo-benzoate

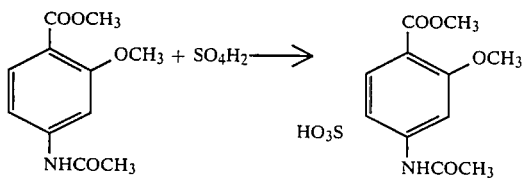

Forty-five liters of acetic acid is placed in a 100 liter reactor. It is agitated and 22.5 kg of methyl 2-methoxy-4-acetamino benzoate is added, after which 30 liters of acetic anhydride is fed in. 5,730 liters of sulfuric acid (d:1.84) is added over 15 minutes. The temperature rises spontaneously to 50°. The ester dissolves. The temperature is brought gradually to 70°. The sulfonic acid crystallises; when 70° C. is reached, the medium is immediately cooled to 20° C. and drained in a centrifugal drier.

The product is washed twice, each time with 8 liters of acetone, then dried in an oven at 50° C.

Properties of product obtained:
Weight: 24.5 kg.
N %: 81.5%.
Melting point: 240° C. with decomposition.
S %: (theory: 10.57%) 10.56%.
White crystals.

2. Methyl 2-methoxy-4-amino-5-sulfo-benzoate

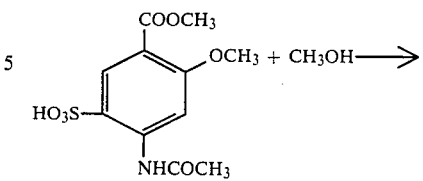

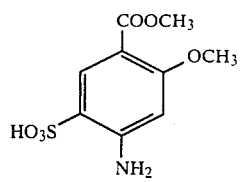

75 liters of methanol is placed in a 100 liter reactor. It is agitated and 24.5 kg of finely ground methyl 2-methoxy-4-acetamino-5-sulfobenzoate is added. The sulfonic acid dissolves; the deacetylated derivative crystallises shortly afterwards. The reaction mixture is left at room temperature for 24 hours, with agitation, so as to complete precipitation. The product is drained in a centrifugal drier, washed twice, with 6 liters of methyl alcohol each time, and dried in a ventilated oven at 50° C.; it has the following properties:

Weight: 20.5 kg-Yield 98%.
Melting point: 240° with decomposition.
S %: 12.10%-Theory 12.26%.

3. Methyl 2-methoxy-4-amino-5-methylsulfamoyl benzoate

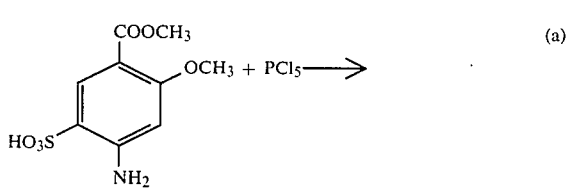

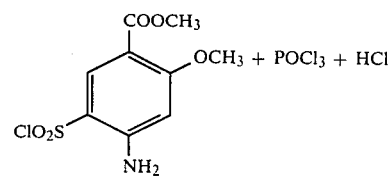

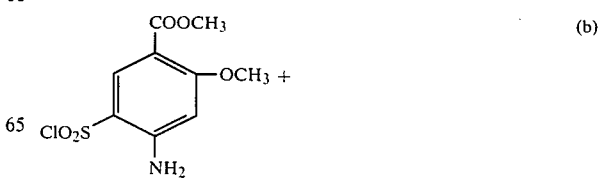

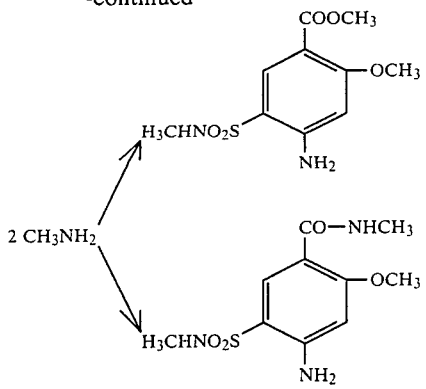

(a) 33.5 liters of acetonitrile is placed in a 100 liter reactor. It is agitated, and 16.8 kg of methyl 2-methoxy-4-amino-5-sulfobenzoate is added; 17.5 kg of phosphorus pentachloride is also added in stages, over approximately 15 minutes. The medium is gradually heated to a reflux temperature of about 80°-85° C. The reaction starts at about 30°, and the liberation of a large amount of gas is noted at this time. In two hours the temperature reaches 80°. The reflux is maintained for 1 hour 30 minutes. The solution is cooled to 55° C.

(b) 95 liters of an aqueous solution containing 35% of methylamine is placed in a 200 liter reactor. It is agitated and cooled to −15° C. The previous solution (sulfochloride) is then poured in slowly and in stages, and the temperature is kept below 10°-15° C. The addition of the solution takes 4 hours, after which the temperature is allowed to rise to 20°. The solution is diluted with 300 liters of water, then filtered through 2 kg of vegetable black. The filtrate is acidified by agitating it with 70 liters of hydrochloric acid (d=1.18). The product gradually crystallises. It is left to stand for 120 hours. It is drained, washed with water and dried in an oven at 50°. 15 kg of the product is thereby obtained.

4. 2-methoxy-4-amino-5-methyl-sulfamoyl benzoic acid

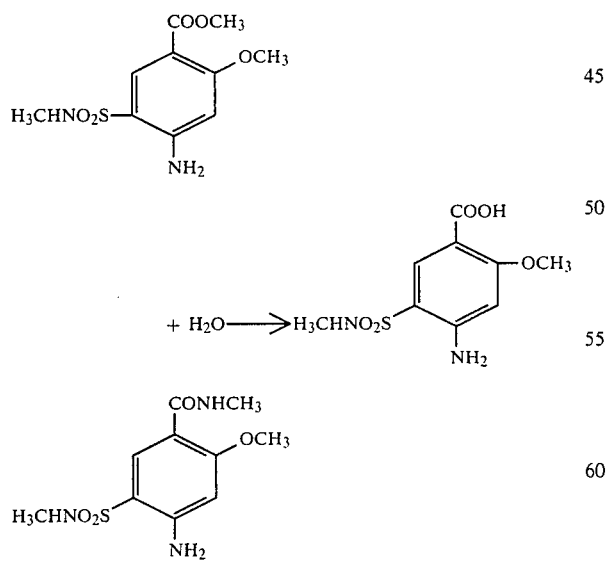

22 liters of water and 22 liters of caustic soda solution are placed in a 100 liter reactor, and 15 kg of the previous product is stirred in. The medium is brought to complete reflux for 20 hours. The liberation of a large amount of methylamine is observed during the first few hours of the reaction. The medium is cooled to 20° C., and the solution is poured into the precipitation tank. 12 liters of water is added. The solution is agitated and acidified to pH 1 with 17 liters of hydrochloric acid (d=1.18). It is necessary to cool the solution while the acid is being poured in. The acid crystallises; it is drained at 20°, washed with water and dried in an oven at 60° C. It has the following properties:

Weight: 12.100 kg.
Melting point: 205° C.
AI: theory 215.4-obtained 212.
S %: theory 12.31%-obtained 12.23%.

40 liters of water and 2.600 kg of sodium bicarbonate are placed in the precipitation tank. They are agitated, and 12.100 kg of 2-methoxy-4-amino-5-methyl-sulfamoyl benzoic acid is added in stages. The acid is dissolved with a great deal of lathering. A small quantity of insoluble gelatinous substance is left, which is removed by filtration under vacuum. The filtrate is acidified with 5.6 liters of hydrochloric acid.

The product crystallises; it is drained, washed with water and dried in an oven at 60° C. The properties of the purified acid are then:

Weight: 11.9 kg.
Melting point: 202° C.
AI: theory 215.4-obtained 215.
S %: theory 12.31%-obtained 12.37%.

5. N(1-allyl-2-pyrrolidinyl-methyl)2-methoxy-4-amino-5-methyl-sulfamoyl bénzamide

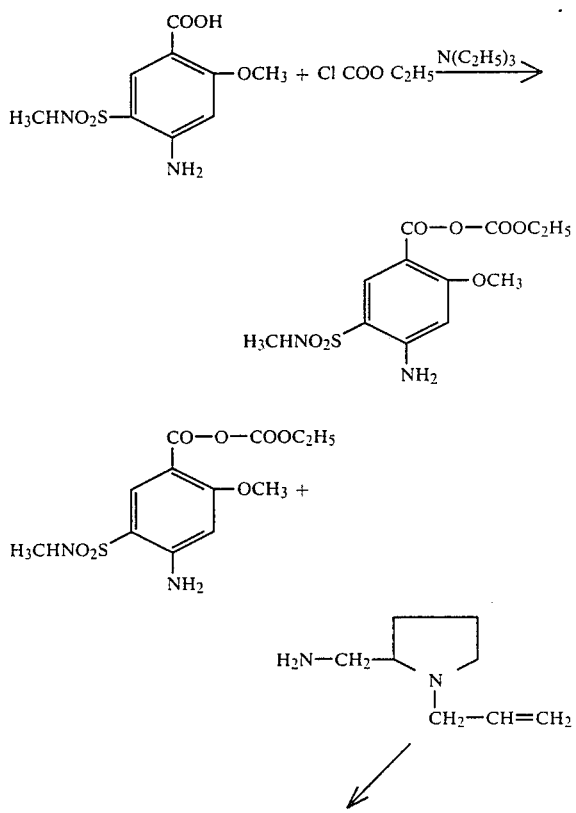

-continued

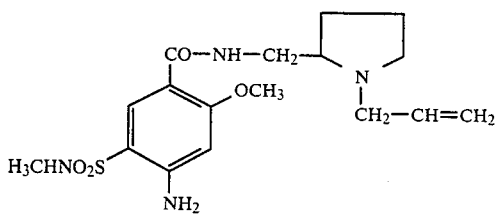

Ten liters of permuted water is placed in a 100 liter reactor. It is agitated, and 5,300 cm³ of triethylamine and 10 kg of 2-methoxy-4-amino-5-methyl-sulfamoyl benzoic acid are fed in. The suspension is heated to about 45° C. to dissolve everything, after which it is cooled to +5° C. by a stream of brine, and 25 liters of acetone is added.

3,670 cm³ of ethyl chloroformate is poured in slowly, (taking 15 minutes) without exceeding a temperature of +10° C. Agitation is continued for 30 minutes at this temperature. 6.4 kg of N-allyl-2-aminomethyl pyrrolidine is poured in slowly (taking 30 minutes) without exceeding +15° C.

The temperature is allowed to rise to 20°, and the medium is agitated for 1 hour at that temperature. The acetone is distilled at normal temperature then under vacuum, without exceeding 60° C. in the mass.

55 liters of water is added, the medium is acidified to pH 3-4 with 7 liters of chemically pure hydrochloric acid, and 1 kg of active carbon black 3S is added. The solution is filtered. The filtrate is made alkaline with 5 liters of ammonia, with vigorous agitation. 10 kg of ice is added, and the agitation is continued for 1 hour. The benzamide first crystallises in liquid form. It is left to stand overnight.

The benzamide is drained at 20°, washed with water and dried in an oven at 60° C. It has the following properties:

Weight: 9 kg.
Yield: 61%.
Melting point: 166°-167° C.

Using a 50 liter reactor, 9 kg of the benzamide previously obtained is dissolved, boiling, in 18 liters of absolute ethyl alcohol. The solution is filtered with 1 kg of vegetable black in a pressure filter. The filtrate is washed with 2 liters of boiling alcohol, then cooled to 10°. The benzamide crystallises. It is drained, washed with cold alcohol and dried in an oven at 60°. It has the following properties:

White crystals. Weight: 8 kg.
Recrystallisation yield: 89%.

Since chromatographic investigation reveals large spots, it will be necessary to carry out two fresh recrystallisations in absolute ethyl alcohol, as a means of arriving at the purified product with the following properties:

White crystals. Weight: 6 kg.
Yield resulting from recrystallisations: 67%.

The process just described produces the benzamide according to the invention with a total yield of 41%. Analysis of the benzamide thus obtained gives the following results:

Melting point: 168.5°-169° C.
Titre: 99.8% % H₂O: 0.1.
%C: theory 53.38-obtained: 53.13.
%H: theory 6.85-obtained: 6.88.
%N: theory 14.65-obtained: 14.65.
%S: theory 8.58-obtained: 8.54.

Taken as a unit, the spectra are compatible with the proposed structure.

Chromatographic investigation reveals the existence of a secondary spot estimated to be from 0.2 to 0.5%.

A pharmacological study has been made of the benzamide according to the invention.

The acute toxicity of the compound was first determined; values for lethal dose 50 with various forms of administration are given below:

| Substance | Administration | $LD_{50}$ male mouse mg/kg (basis) |
|---|---|---|
| Benzamide According to the invention | Intravenous | 44 |
| | Intra-peritoneal | 184 |
| | Subcutaneous | 204 |
| | Per os | 3600 |

The researchers were looking for the effects of the benzamide on the central nervous system and particularly for any neuroleptic action. Tests showed the compound to have very little depressive action, thus:

it only very slightly reduces the spontaneous motility of the mouse, even in high doses (Table 1)

it does not extend the duration of barbituric hypnosis (Table 2).

TABLE 1

| | | Spontaneous motility of mouse: inhibiting effect observed at maximum dose administered | |
|---|---|---|---|
| Product | Administration | WINTER & FLATAKER method | Activograph method |
| Benzamide according to the invention | I.P. | 26% effect at 80 mg/kg | 22% at 80 mg/kg |
| | P.O. | 20% effect at 300 mg/kg | 25% at 300 mg/kg |

TABLE 2

| Product | Administration | Dose mg/kg | Time of hypnosis, mice treated Time of hypnosis, control mice |
|---|---|---|---|
| Benzamide according to the invention | I.P. | 80 | 1.6 |

N.B. The barbiturate used is pentobarbital in a dose of 60 mg/kg given intraperitoneally.

Unlike conventional neuroleptics, the compound does not cause catalepsy in the rat, even in a dose of 200 mg/kg given subcutaneously, and does not counteract the stereotypic movements of the rat caused by dopaminergic agonistes, such as apomorphine or amphetamine.

The benzamide has no anticonvulsive action when the convulsions are caused by electric shock, a chemical agent (pentetrazol, nicotine) or an auditory stimulus.

The analgesic action of the benzamide, in a single dose, is weak in respect of the pain caused in a mouse by a mechanical, chemical or heat stimulus.

The effects of the benzamide on the cardiovascular system were studied in a dog anaesthetised with chloralose, with the following results:

The compound causes a drop in arterial pressure proportional to the dose administered (Table 3)

The compound does not change the hypotensive response to acetylcholine or to excitation of the vagus nerve. The fact that the benzamide has no anticholinergic action was confirmed by a test in vitro on the isolated ileum of a guinea pig.

The compound reduces the hypertensive responses caused by catecholamines (adrenalin and noradrenalin), by blocking the carotid arteries and by small doses of nicotine (Table 4)

The compound reduces the hypertensive response to serotonin in a dog, the dog being anaesthetised and further treated with a ganglioplegic, chlorisondamine, which stabilises the response (Table 5)

| Cumulative dose of benzamide according to the invention (mg/kg/I.V.) | Variations in arterial pressure relative to initial pressure |
|---|---|
| 0.5 | −21% |
| 1 | −32% |
| 2 | −36% |
| 4 | −48% |
| 8 | −54% |
| 16 | −59% |
| 32 | −58% |

TABLE 4

| Methods | Cumulative dose of benzamide according to the invention (mg/kg/I.V.) | |
|---|---|---|
| Orthosympathetic system | | |
| Blocking of carotid | 0.5 | 0% |
| arteries | 1 | R = 30% |
| (for 30 seconds) | 2 | R = 43% |
| | 4 | R = 48% |
| % reduction relative | 8 | R = 86% |
| to control hyper- | 16 | R = 90% |
| tension (R) | 32 | R = 100% |
| Adrenalin | 0.5 | R = 5% |
| % reduction relative | 1 | R = 3% |
| to control hyper- | 2 | R = 4% |
| tension (R) | 4 | R = 21% |
| | 8 | R = 40% |
| | 16 | R = 68% |
| | 32 | R = 84% |
| Noradrenalin | 0.5 | R = 21% |
| % reduction relative | 1 | R = 13% |
| to control hyper- | 2 | R = 30% |
| tension (R) | 4 | R = 30% |
| | 8 | R = 40% |
| | 16 | R = 49% |
| | 32 | R = 66% |
| Nicotine | 0.5 | 0% |
| % reduction of ortho | 1 | 0% |
| sympathetic | 2 | 0% |
| component (R) | 4 | 0% |
| | 8 | 0% |
| | 16 | R = 49% |
| | 32 | R = 79% |

TABLE 5

| Product | Doses in mg/kg I.V. | Serotonin in μg/kg I.V. | % inhibition of hypertension after | | | | | |
|---|---|---|---|---|---|---|---|---|
| | | | 3 mn | 30 mn | 1 h | 1 h 30 | 2 h | 3 h |
| Benzamide according to the invention BATCH 1 | 5 | 25 | 62% | 63% | 51% | 51% | 40% | — |
| | 1 | 37.5 | 22% | 8% | — | — | — | — |
| Benzamide according to the invention BATCH 2 | 5 | 25 | 78% | 65% | 48% | 43% | 33% | 33% |
| | 1 | 25 | 36% | 11% | 0 | — | — | — |

Since the results set out in Table 5 above showed the benzamide according to the invention counteracting the pressing effect of serotonin, search was made for other interactions with serotonin.

Tests showed that the benzamide according to the invention:
inhibited contraction of the isolated uterus of a rat, produced by serotonin. The contraction inhibiting dose 50 is of the order of 0.2 mg/l.

had a protective action in respect of the gastric ulcer producing effect of serotonin in the rat, the effective dose 50 being of the order of 3 mg/kg given subcutaneously.

reduced the oedema in the paw of a rat which had received an intraplantar injection of 0.01 mg of serotonin. The effective dose 50 is of the order of 4 to 6 mg/kg when administered by intraplantar injection and 200 mg when given orally.

Finally, researchers looked for interaction between the benzamide according to the invention and histamine, in the arterial pressure of an anaesthetised dog and the isolated ileum of a guinea pig. No anti-histamine properties were revealed by the two tests.

Given the pharmacological profile of the benzamide according to the invention, as defined by the tests reported above, it became apparent that the antiserotonin action component on the one hand and the circulatory effect on the other might give the benzamide a therapeutic importance in migraines, which is precisely the area where vasomotor disorders caused by adrenergic and serotoninergic transmissions appear to arise (the latter intermediary may also act through other mechanisms). The correctness of this hypothesis was demonstrated by clinical research.

The first clinical pharmacological investigation consisted of exploring the cerebral haemodynamics of migraine patients by a non-invasive method, through recording the pulsatility of the cerebral arteries. The graphs plotted showed permanent anomalies relative to a normal control patient between attacks, thus enabling the migraine patient to be defined objectively. Graphs were thus plotted after the benzamide according to the invention had been absorbed by migraine patients.

In a treatment by intramuscular injection of a single 100 mg dose of the benzamide, the graph moves towards normalisation in 2 hours. This is maintained under treatment with repeated doses (150 mg/day) given orally for 3 weeks.

Once the action of the benzamide according to the invention in correcting anomalies in the cerebral haemodynamics of migraine sufferers had been demonstrated, clinical investigations were developed comprising:

(1) A comparative study, by a crossed double blind method, the reference product being oxetorone, which is medically known, applied to migraine. The study covered 63 migraine patients, the two treatments being applied for 30 days with an adequate interruption between sequences. The dose of benzamide was 150 mg per day, and that of oxetorone 120 mg, as recommended by the literature. Analysis of the results, allowing both for therapeutic effectiveness and tolerance of the treatment, indicates that the benzamide according to the invention is statistically superior to oxetorone ($P<0.05$).

(2) A comparative study with Pizotifene, an anti-histamine and antiserotonin compound which is also used in the basic treatment for migraine.

The study covered 17 patients suffering true attacks of migraine of regular frequency, which thus enabled the effectiveness of the treatment to be assessed from the number and intensity of attacks during a period of one month.

The benzamide according to the invention was applied orally in a dose of 150 mg per day, in three times. The Pizotifene was also administered orally, with the progressive dosage recommended for the product (0.73 mg$\times$1 for 3 days-0.73 mg$\times$2 for 3 days-0.73 mg$\times$3 for 24 days).

The patients were distributed at random between the treatments.

Analysis of the results confirms the action of the benzamide according to the invention, which is shown to be more effective than the second reference compound ($P\#0.02$).

(3) An open investigation covering 80 patients, who were followed in out-patient treatment with 150 mg of benzamide per day, given orally in 3 doses:

79% success was recorded, and in particularly severe cases of "accompanied" migraines the remission transformed the social life of the patient. General tolerance of the treatment was very satisfactory.

In conclusion, the benzamide according to the invention has a therapeutic importance which is demonstrated in the basic treatment of migraine.

We claim:

1. As a new product, N-(1-allyl-2-pyrrolidinylmethyl)2-methoxy-4-amino-5-methylsulfamoyl benzamide, quaternary ammonium salts thereof, N-oxides thereof, optical isomers thereof and their pharmacologically acceptable acid addition salts.

* * * * *

UNITED STATES PATENT AND TRADEMARK OFFICE
CERTIFICATE OF CORRECTION

PATENT NO.   : 4,550,179
DATED        : October 29, 1985
INVENTOR(S)  : Jacques Perrot et al.

It is certified that error appears in the above-identified patent and that said Letters Patent is hereby corrected as shown below:

The term of this patent subsequent to September 20, 2000, has been disclaimed.

Signed and Sealed this

Seventeenth Day of December 1985

[SEAL]

Attest:

Attesting Officer

DONALD J. QUIGG

Commissioner of Patents and Trademarks